United States Patent
Kang et al.

(10) Patent No.: US 7,635,330 B2
(45) Date of Patent: Dec. 22, 2009

(54) FLUORESCENT ENDOSCOPE SYSTEM HAVING IMPROVED IMAGE DETECTION MODULE

(75) Inventors: Uk Kang, Gunpo-si (KR); Garry V. Papayan, St. Petersburg (RU)

(73) Assignee: Korea Electrotechnology Research Institute, Gyongsangham-Do (KR)

( * ) Notice: Subject to any disclaimer, the term of this patent is extended or adjusted under 35 U.S.C. 154(b) by 782 days.

(21) Appl. No.: 11/072,995

(22) Filed: Mar. 4, 2005

(65) Prior Publication Data

US 2005/0203343 A1 Sep. 15, 2005

(30) Foreign Application Priority Data

Mar. 5, 2004 (KR) ................. 10-2004-0014944

(51) Int. Cl.
*A61B 1/06* (2006.01)
(52) U.S. Cl. .................. 600/160; 600/109
(58) Field of Classification Search ............... 600/109, 600/160, 165, 178, 180, 181; 348/68, 69
See application file for complete search history.

(56) References Cited

U.S. PATENT DOCUMENTS

| | | | | |
|---|---|---|---|---|
| 5,749,830 | A * | 5/1998 | Kaneko et al. | 600/160 |
| 5,877,806 | A * | 3/1999 | Kawano | 348/219.1 |
| 6,602,186 | B1 * | 8/2003 | Sugimoto et al. | 600/126 |
| 7,179,222 | B2 * | 2/2007 | Imaizumi et al. | 600/109 |
| 7,226,412 | B2 * | 6/2007 | Ueno et al. | 600/178 |
| 2002/0062061 | A1 * | 5/2002 | Kaneko et al. | 600/118 |
| 2002/0093563 | A1 * | 7/2002 | Cline et al. | 348/65 |
| 2002/0175993 | A1 * | 11/2002 | Ueno et al. | 348/68 |
| 2003/0078477 | A1 * | 4/2003 | Kang et al. | 600/178 |
| 2004/0186345 | A1 * | 9/2004 | Yang et al. | 600/102 |
| 2004/0230098 | A1 * | 11/2004 | Farkas et al. | 600/178 |

FOREIGN PATENT DOCUMENTS

KR 0411631 1/2003

* cited by examiner

*Primary Examiner*—John P Leubecker
*Assistant Examiner*—Philip R Smith
(74) *Attorney, Agent, or Firm*—The Webb Law Firm

(57) ABSTRACT

Disclosed is an improved fluorescent endoscope system having reduced factors that cause errors during diagnosis based on quantitative evaluation of fluorescent intensity for improved accuracy of fluorescent endoscopic diagnosis. The fluorescent endoscope system includes an optical source module for providing white light or excitation light; an endoscope assembly having an optical transmission path for transmitting light provided from the optical source module to a diagnostic object and an optical detection module for transmitting reflection light and fluorescent light from the diagnostic object; an optical path split means for splitting the path of the reflection light and fluorescent light transmitted from the endoscope assembly; and a two-chip integration image detection module having a first optical detection chip for detecting the reflection light and outputting a first optical detection signal, a second optical detection chip for detecting the excitation light and outputting a second optical detection signal, a gain control unit for controlling a signal amplification gain value to adjust the brightness of an image detected by the first optical detection chip, a first amplification unit for amplifying the first optical detection signal according to the signal amplification gain value, and a second amplification unit for amplifying the second optical detection signal according to a changing ratio of the signal amplification gain value.

26 Claims, 9 Drawing Sheets

PRIOR ART

FLUORESCENT LIGHT (a)

REFLECTION LIGHT (b)

FLUORESCENT ENDOSCOPE SYSTEM HAVING IMPROVED IMAGE DETECTION MODULE

BACKGROUND OF THE INVENTION

1. Field of the Invention

The present invention relates to a fluorescent endoscope system and a method for imaging diagnostic objects using the same, and more particularly to a fluorescent endoscope system having an improved image detection module for accurate and efficient diagnosis of tumors in the human body and a method for imaging in vivo diagnostic objects using the same.

2. Description of the Prior Art

As generally known in the art, a vesical fluorescent endoscope has been developed by Karl Storz GmgH, Germany, and used for vesical tumor diagnosis. It uses an optical source of white light and provides detailed observation of the surface of an internal organ as a normal endoscope system. Furthermore, it also uses an optical source (e.g., D-LIGHT) of blue light as excitation light, which is composed of a xenon lamp and an optical fiber, and provides fluorescent observation of dubious parts induced by a contrast medium (e.g., ALA).

The above fluorescent endoscope provides visual inspection and fluorescent observation of dubious parts with Endovision Telecom SL-PDD, which is a TV camera having a single high-sensitivity color chip. In a fluorescent diagnostic mode, an optical filter is positioned in front of the TV camera to interrupt excitation light reflected from a diagnostic object. The optical filter is designed in such a manner that a part of the reflected excitation light reaches the camera detector because, if the reflected excitation light is completely interrupted, the observer (e.g., a physician) cannot correctly recognize from where fluorescent light is generated. Such partial transmission of excitation light through the optical filter helps the physician to grasp the position and direction of the diagnostic object by observing the background portion which does not emit fluorescent light on the screen in the fluorescent diagnostic mode.

However, the above-mentioned conventional fluorescent endoscope system has problems as follows: the color TV camera of the fluorescent endoscope system, which basically has lower sensitivity than monochrome cameras, cannot accurately perceive faint fluorescent light emitted from the diagnostic object and, in particular, cannot be used when an endoscope having a small aperture ratio is necessary. Furthermore, optical noise increases and faint fluorescent light cannot be perceived, because reflected excitation light is partially transmitted. The color TV camera used in the above fluorescent endoscope system also has non-linear characteristics regarding optical signals. In summary, poor sensitivity to fluorescent light and existence of optical noise make diagnosis through quantitative fluorescent observation impossible.

In order to solve these problems, a fluorescent endoscope system having two channels has been proposed in Korean Registered Patent No. 0411631 of Uk Kang and G. V. Papayan, entitled "FLUORESCENT ENDOSCOPE SYSTEM AND METHOD FOR IMAGING DIAGNOSTIC OBJECTS USING THE SAME." The proposed system includes an endoscope assembly having an optical cable and an optical source module connected to the assembly. The light module irradiates white light for use in a normal endoscope mode and/or excitation light of short wavelength for use in a fluorescent inspection mode to a diagnostic object through the optical cable. Images of the diagnostic object are transmitted from the distal end of the endoscope assembly to the projection objective lens positioned on the proximal end thereof through the optical cable. A foldable dichroic optical splitter is positioned behind the projection objective lens as an optical path split means. As the mode changes between a normal endoscope mode and a fluorescent inspection mode, the position of the dichroic optical splitter is mechanically adjusted and the optical source positioned on the optical source module can be modified. The mode can be arbitrarily switched with a remote switch (e.g., a pedal).

In the fluorescent inspection mode, light inputted via the optical cable is split by the dichroic optical splitter into two paths leading to two TV cameras, respectively. The TV camera positioned in the first path has a color optical detection chip and is used to perceive images created by reflected excitation light. The TV camera positioned in the second path has a high-sensitivity monochrome (black and white) optical detection chip and is used to sense fluorescent images. An optical shield filter is positioned in front of the high-sensitivity monochrome optical detection chip in the second path to transmit light having fluorescent wavelength only. Signals from both TV cameras are transmitted to a computer. The computer's processor is programmed to control the operation of the TV cameras and process and analyze the images obtained from the TV cameras. Each frame from both TVs is displayed on a monitor.

Before endoscopic inspection is performed with the above endoscope system, the system is calibrated with a comparative fluorescent sample. For calibration, the endoscope assembly is positioned adjacent to the surface of the comparative fluorescent sample and light is irradiated. The resulting image (as shown in FIG. 7) of reflected light and fluorescent light are stored in the computer. The stored data is used to compensate for the irregularity of illumination to the diagnostic object and that of fluorescent images caused by the spatial difference of the degree of light collection in the field of view of the endoscope. The data is also used to determine when to replace the lamp and adjust the sensitivity of the equipment considering the aging of the lamp.

In order to perform a diagnosis based on quantitative analysis of fluorescent intensity, it is necessary to reduce the light measurement error caused by the change in distance from the distal end of the endoscope to the surface of the diagnostic object. To this end, a tool 36 is pushed out through a tool passage formed in the endoscope assembly 30 as shown in FIG. 3 and measurement is performed while maintaining a reference distance between the tool and the diagnostic object. Quantitative analysis of fluorescent intensity is preformed by analyzing the histogram of signal intensity distribution on the video frame.

The above-mentioned fluorescent endoscope system has problems as follows: in order to recognize from what part of the diagnostic object the fluorescent images are generated, both reflected excitation light and fluorescent light must be viewed on the same screen. If the reflected excitation light is partially transmitted to the high-sensitivity optical detection chip for sensing fluorescent light to this end, however, the accuracy of quantitative analysis deteriorates. The reflected excitation light and the fluorescent light are preferably detected via different paths. However, images of the reflected excitation light and those of the fluorescent light, which have been obtained separately, must be superimposed and displayed on the same screen. Although the above fluorescent endoscope system according to the prior art uses two cameras to separately detect reflected excitation light and fluorescent light for improved accuracy of quantitative analysis, the cameras are operated asynchronously and, when image signals of reflected excitation light and fluorescent light obtained from both asynchronously operated cameras are successively inputted to a computer via a PCI bus, a number of frames are lost due to difference in frame timing. In addition, the system speed decreases when images from reflected excitation light and fluorescent light are displayed on a monitor. Therefore, the problem of timing difference of the image data obtained from both cameras must be resolved. In order to display superimposed images, the size of images detected from both cameras must coincide. When signals obtained from different cameras are separately processed according to the prior art, however, such coincidence is difficult to occur.

In the above fluorescent endoscope system, the distance between the distal end of the endoscope and the diagnostic object is mechanically maintained with a tool for quantitative analysis of fluorescent intensity in a fluorescent inspection mode. Such mechanical maintenance of distance is vulnerable to errors resulting from diagnostic environments (e.g., fine vibration) and has limited diagnostic accuracy.

In order to independently drive two cameras, furthermore, separate driving circuit and data process module must be installed. This makes the system very complicated.

SUMMARY OF THE INVENTION

Accordingly, the present invention has been made to solve the above-mentioned problems occurring in the prior art, and an object of the present invention is to provide an improved fluorescent endoscope system having first and second optical detection chips integrated in a single camera module to obtain images of excited reflection light and fluorescent light with the same timing for minimized frame loss and efficient composition and display of superimposed images.

Another object of the present invention is to provide a fluorescent endoscope system capable of compensating for the change of fluorescent intensity, which depends on the distance from the diagnostic object to the distal end of the endoscope module, using signals of reflected excitation light for accurate diagnosis independent of the distance.

Another object of the present invention is to provide a fluorescent endoscope system capable of processing data to compensate for the inaccuracy of fluorescent intensity caused by the geometry of a diagnostic object (e.g., an organ), in addition to the spatial difference in illumination and degree of light collection of the endoscope as in the prior art.

Another object of the present invention is to provide an improved fluorescent endoscope system having reduced factors that cause errors during diagnosis based on quantitative evaluation of fluorescent intensity for improved accuracy of fluorescent endoscopic diagnosis.

In order to accomplish these objects, there is provided a fluorescent endoscope system including an optical source module for providing excitation light; an endoscope assembly having an optical transmission path for transmitting light provided from the optical source module to a diagnostic object and an optical detection module for transmitting reflection light and fluorescent light from the diagnostic object; an optical path split means for splitting the path of the reflection light and fluorescent light transmitted from the endoscope assembly; and a two-chip integration image detection module having a first optical detection chip for detecting the reflection light and outputting a first optical detection signal, a second optical detection chip for detecting the excitation light and outputting a second optical detection signal, a gain control unit for controlling a signal amplification gain value to adjust the brightness of an image detected by the first optical detection chip, a first amplification unit for amplifying the first optical detection signal according to the signal amplification gain value, and a second amplification unit for amplifying the second optical detection signal according to a changing ratio of the signal amplification gain value.

According to another aspect of the present invention, there is provided a fluorescent endoscope system including an optical source module for providing excitation light; an endoscope assembly having an optical transmission path for transmitting light provided from the optical source module to a diagnostic object and an optical detection module for transmitting reflection light and fluorescent light from the diagnostic object; an optical path split means for splitting the path of the reflection light and fluorescent light transmitted from the endoscope assembly; a two-chip integration image detection device having a first optical detection chip for detecting the reflection light and outputting a first optical detection signal for each frame, a second optical detection chip for detecting the excitation light and outputting a second optical detection signal for each frame, and a digital control unit for providing the first and second optical detection chips with a common synchronization signal so that the timing of each frame of the first and second optical detection signals coincides; and an image composition unit provided with an input switch having a first state for selectively receiving the first optical detection signal and a second state for selectively receiving the second optical detection signal and adapted to alternatively receive data of some frames of output of the first optical detection signal and data of some frames of output of the second optical detection signal to convert them and display a composite image.

According to another aspect of the present invention, there is provided a fluorescent endoscope system including an optical source module for providing excitation light; an endoscope assembly having an optical transmission path for transmitting light provided from the optical source module to a diagnostic object and an optical detection module for transmitting reflection light and fluorescent light from the diagnostic object; an optical path split means for splitting the path of the reflection light and fluorescent light transmitted from the endoscope assembly; an image detection device for detecting the reflection light and the fluorescent light, respectively; and a data processing unit which uses the ratio of image brightness (L1) of the reflection light of a first point to image brightness (L2) of the reflection light of a second point in the field of view of the endoscope and compensates for obtained image brightness (F2) of the fluorescent light of the second point based on image data obtained by the image detection device.

BRIEF DESCRIPTION OF THE DRAWINGS

The above and other objects, features, and advantages of the present invention will be more apparent from the following detailed description taken in conjunction with the accompanying drawings, in which.

DETAILED DESCRIPTION OF THE PREFERRED EMBODIMENTS

Figure 1:
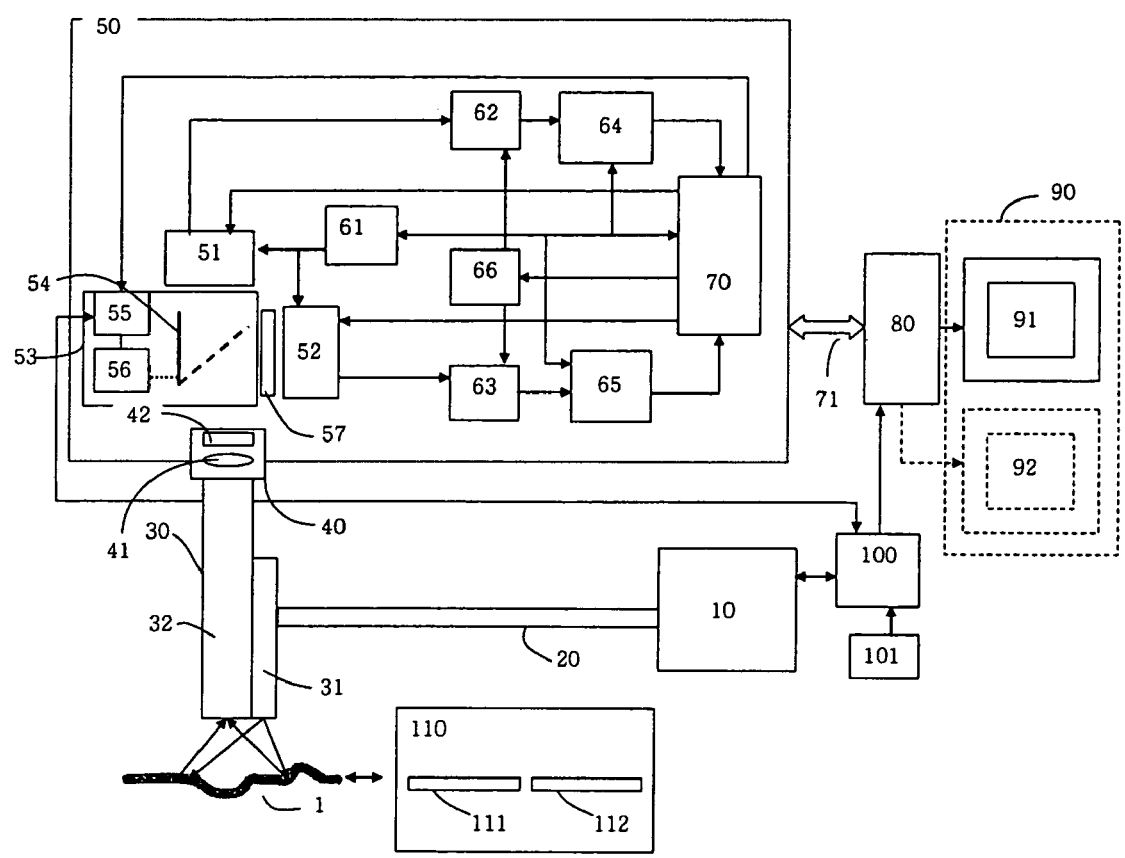
FIG. 1 shows the construction of a fluorescent endoscope system according to a preferred embodiment of the present invention.

Hereinafter, a preferred embodiment of the present invention will be described with reference to the accompanying drawings. In the following description and drawings, the same reference numerals are used to designate the same or similar components, and so repetition of the description on the same or similar components will be omitted.

FIG. 1 is a block diagram showing the construction of a fluorescent endoscope system according to a preferred embodiment of the present invention. The fluorescent endoscope system includes a composite optical source module 10 connected to an optical source cable 31 provided in the endoscope. The composite optical source module 31 uses incoherent light as an optical source and provides white light for normal visual observation of a diagnostic object 1 (in a normal endoscope mode) or short-wavelength light for fluorescent excitation to simultaneously observe fluorescent light and reflected excitation light (in a fluorescent observation mode).

The optical source module 10 is provided with a optical source to provide illumination light and excitation light. For example, illumination light and excitation light may be separately provided by two lamps. Alternatively, illumination light is provided by a metal-halide lamp and excitation light is provided by a mercury lamp. In necessary, illumination light and excitation light may be provided by a single lamp which may be a metal-halide lamp, an LED, or a xenon lamp. When contrast medium ALA is used to diagnose cancer, excitation light preferably has a spectrum range of 380-580 nm and fluorescent light generally has a wavelength of 600 nm or more. However, the wavelength range may vary depending on the kind of used contrast medium and the optical system including various optical sources and filters may be suitably configured according to the wavelength range.

When the user wants to toggle a normal endoscope mode (first mode) into a fluorescent observation mode (second mode) or vice versa, he may input a signal via a computer 80 which is then transmitted through a control unit 70 or he may use an external switch, such as a pedal 101, for toggling. A toggling signal transmitted via the computer 80 is transmitted to a driving unit 55 or a toggling signal through the external switch 101 is transmitted to an exchange block 100, so that the optical source 10 and the driving unit 55 modifies the kind of the optical source and the position of a dichroic optical splitter 54 according to the inspection condition. For example, the driving unit 55 may be made up of a solenoid.

Images emitted from the diagnostic object 1 are transmitted via an image transmission cable 32 of the endoscope assembly 30. The endoscope assembly 30 may be a flexible or hard endoscope and may be an optical fiber or an electronic endoscope, but is independent of the type of endoscope. Light transmitted through the endoscope assembly 30 reaches an optical path split means 53. The optical path split means 53 includes a dichroic optical splitter 54, an driving unit 55 for driving the dichroic optical splitter 54, and a control block 56 based on the driving unit 55. The optical path split means 53 properly controls the path of reflected excitation light and fluorescent light according to the mode of the fluorescent endoscope system.

The fluorescent endoscope system of the present embodiment has a two-chip integration image detection module 50 which includes first and second optical detection chips 51 and 52 mounted thereon, an optical detection chip timing control block 61 for common control of the chips 51 and 52, first and second video signal analog processing blocks 62 and 63, first and second analog-digital converters 64 and 65, a digital-analog converter 66 for converting digital control input signals into analog signals, and a control unit 70. The control unit 70 transmits data to the computer 80 and, for example, may support IEEE1394 standard. In this case, a bus unit 71 supporting the same standard must be used.

Together with the optical path split means 53, the two-chip integration image detection module 50 is coupled to the endoscope assembly 30 via an optical coupling means 40 including a projection objective lens 41 for projecting images on the optical detection surface of the first and second optical detection chips 51 and 52. The optical coupling means 40 may has a spatial low-pass filter 42 which interrupts a specific spatial frequency to remove moiré effect. The spatial low-pass filter 42 is preferably adapted to rotate about an optical axis for fine adjustment in the direction of the optical fiber bundle arranged in the flexible endoscope.

The two-chip integration image detection module 50 may have an optical shield filter 57 positioned in front of the second optical detection chip so that only transmit fluorescent light is transmitted for better sensitivity of fluorescent light.

The first optical detection chip 51 is a color optical detection device, such as CCD, and the second optical detection chip 52 is a high-sensitivity monochrome optical detection device. Light transmitted to the image detection module 50 in a fluorescent observation mode is incident on the dichroic optical splitter 54. Reflected excitation light of the light incident on the dichroic optical splitter 54 passes through the dichroic optical splitter 54 and is transmitted to the first optical detection chip 51 and fluorescent light thereof is reflected by the dichroic optical splitter 54 and is transmitted to the second optical detection chip 52. The dichroic optical splitter 54 is configured in such a manner that reflected light spectrum corresponds to fluorescent emission spectrum. An optical shield filter 57 is positioned in front of the second optical detection chip 52 to allow only fluorescent light to pass through and interrupt reflected excitation light. The dichroic optical splitter 54 is positioned out of the optical path in a normal endoscope mode and light is transmitted only to the first optical detection chip 51.

The positional change of the dichroic optical splitter 54 according to mode toggling is mechanically performed by the driving unit 55 and the control block 56 based on the driving unit 55. The position or angle of the dichroic optical splitter 54 is changed together with the optical source in the optical source module 10 according to mode toggling. In a fluorescent observation mode, the optical source module 10 provides excitation light and the dichroic optical splitter 54 is positioned in the optical path.

In the fluorescent endoscope system shown in FIG. 1, scanning of the first and second optical detection chips 51 and 52 is performed with timing which is synchronized by the optical detection chip timing control block 61. First and second optical detection signals outputted from the first and second optical detection chips 51 and 52 are subjected to amplification and analog signal processing by the first and second video signal analog processing blocks 62 and 63, respectively. The first and second analog-digital converters 64 and 65 then convert analog image data into digital data and the control unit 70 creates and receives various digital signals necessary for the operation and data processing of the system. For example, the control unit 70 sends signals to the driving unit 55 to change the position of the dichroic mirror constituting the dichroic optical splitter 54, sends signals to the first and second optical detection chips 51 and 52 to control the electronic shutter value, or exchanges synchronization signals with the optical detection chip timing control block 61 and sends signals for determining charge accumulation time to the optical detection chips 51 and 52. Furthermore, the control unit 70 transmits signals for controlling the amplification coefficient of the first and second video signal analog processing blocks 62 and 63 via the digital-analog converter 66 and receives video signal values of a digital type from the first and second analog-digital converters 64 and 65 and transmit them to the computer 80 via a high-speed bus 71 (e.g., standard IEEE-1394). The control unit 70 may also have a block to control the image detection module via a low-speed bus (e.g., standard I2C).

Image signals on each pixel of the first and second optical detection chips 51 and 52 are digitalized (e.g., 8 bit) and transmitted to the computer 80 via the bus 71 to be used for display of images, composition of superimposed images, analysis and storage of data. If images of excited reflection light and fluorescent light outputted from the first and second optical detection chips 51 and 52 are superimposed and displayed on the same screen, the user can accurately recognize the direction and direction of objects that emit fluorescent light without any degradation of the accuracy of quantitative analysis of fluorescent images.

The computer 80 controls the operation of the fluorescent endoscope system, processes and analyzes data, and provides a suitable user interface screen.

White and fluorescent samples 111 and 112 are provided as reference specimens to compensate for the irregularity of illumination to the diagnostic object and that of fluorescent images caused by the spatial difference of the degree of light collection in the field of view of the endoscope, as mentioned above. The white sample 111 is a diffusive reflector having a uniform reflectivity in the spectrum range of visible rays and the fluorescent sample 112 has an emission spectrum similar to the fluorescent spectrum of the diagnostic object. The fluorescent brightness emitted from the fluorescent sample 112 is set to approach the maximum fluorescent brightness of the diagnostic object. An auxiliary monitor 92 may be additionally used to separately display color images outputted from the first optical detection chip 51.

Figure 5:
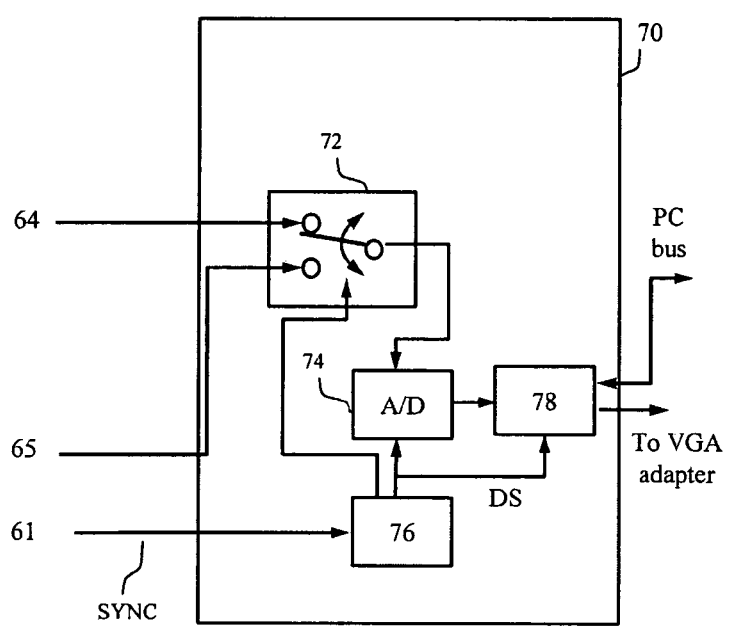
FIG. 5 shows the detailed construction of another embodiment of the present invention and a block diagram of an image frame having minimized data loss based on the same.
Figure 5:
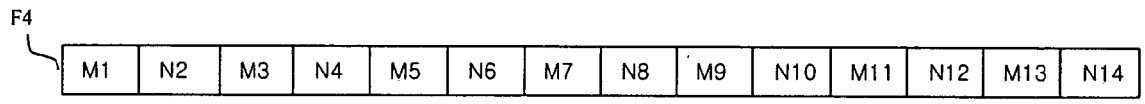

FIG. 5 shows in brief the construction of a second embodiment of the present invention. The same components as in the embodiment shown in FIG. 1 are omitted and only the control unit 70 is shown in detail. In order to superimpose reflected excitation light and fluorescent light, each frame of the first and second optical detection signals is alternatively received by the control unit 70 as time elapses in the second embodiment, so that images of excitation light and fluorescent light are alternative displayed on the screen as shown in FIG. 5. As a result, the user regards two images as being superimposed and displayed on the screen, because alternation of excited reflection light and fluorescent light occurs in a very short period of time per each frame.

To this end, the control unit 70 has an input switch 72 which toggles between a first state for selectively receiving a first optical detection signal and a second state for selectively receiving a second optical detection signal. The input switch 72 alternatively receives data of a part of the frame of the first optical detection signal and data of a part of the frame of the second optical detection signal to display superimposed images.

Figure 4:
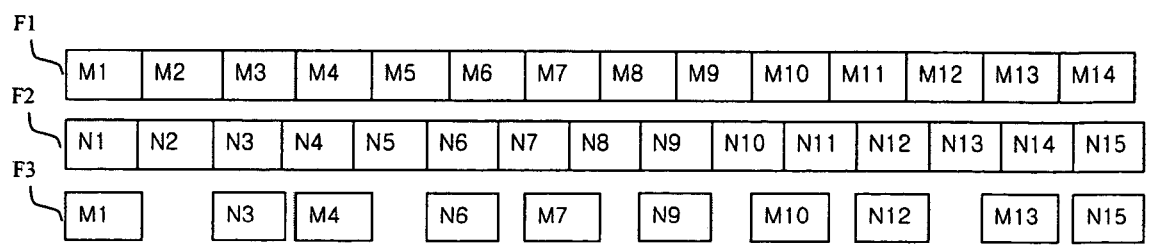
FIG. 4 shows the loss of image frame data when images are processed in an asynchronous mode according to the prior art.

FIG. 4 shows the loss of data occurring when images obtained from two cameras operated asynchronously are composed and displayed on the same screen according to the prior art. Each frame F1 of the image signal of reflective excitation light is not synchronized with each frame F2 of the image signal of fluorescent light and the signals have different frame cycles (for example, the first image signal has a frame cycle of 14 Hz and the second image signal has a frame cycle of 15 Hz, as shown in FIG. 4). When first and second optical detection signals S1 and S2 are to be alternatively inputted with an input switch as shown in FIG. 5, the switch 72 of the image composition unit receives a frame M1 of the first optical detection signal and sends it to an A/D converter 74 positioned behind as shown in FIG. 4, in order to obtain a superimposed and composed image signal F3. The A/D converter 74 is integral with the control unit 70 in this case and the first and second analog-digital converters 64 and 65 positioned in front of the control unit as in the case of FIG. 1 are unnecessary. When a frame of the first optical detection signal is completely received, the second frame N2 of the second optical detection signal has already been initiated. The image detection unit then receives the third frame N3 instead. As a result, the frame of the superimposed image consists of M1, N3, M4, . . . as shown in the bottom line of FIG. 4 and data loss occurs to parts of the frame. According to the fluorescent endoscope system according to the present invention, however, the first and second optical detection chips 51 and 52 are driven based on a common synchronization signal SYNC and have the same timing. Therefore, superimposed images can be obtained without any data loss as shown in the bottom of FIG. 5.

Figure 2:
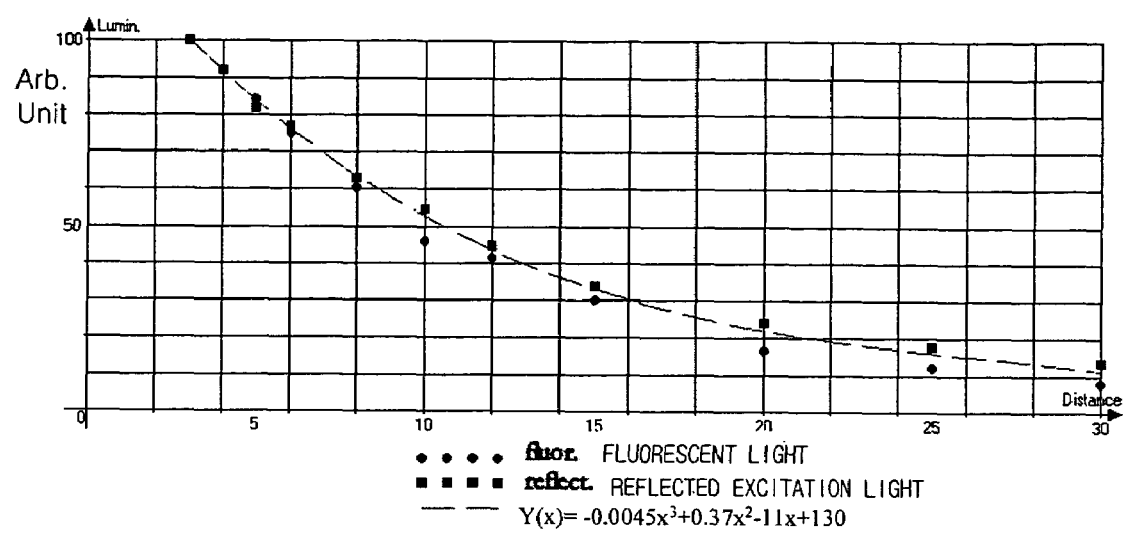
FIG. 2 shows the change in comparative brightness of fluorescent light and reflected excitation light detected when the distance from the distal end of the endoscope to a diagnostic object changes.
Figure 3:
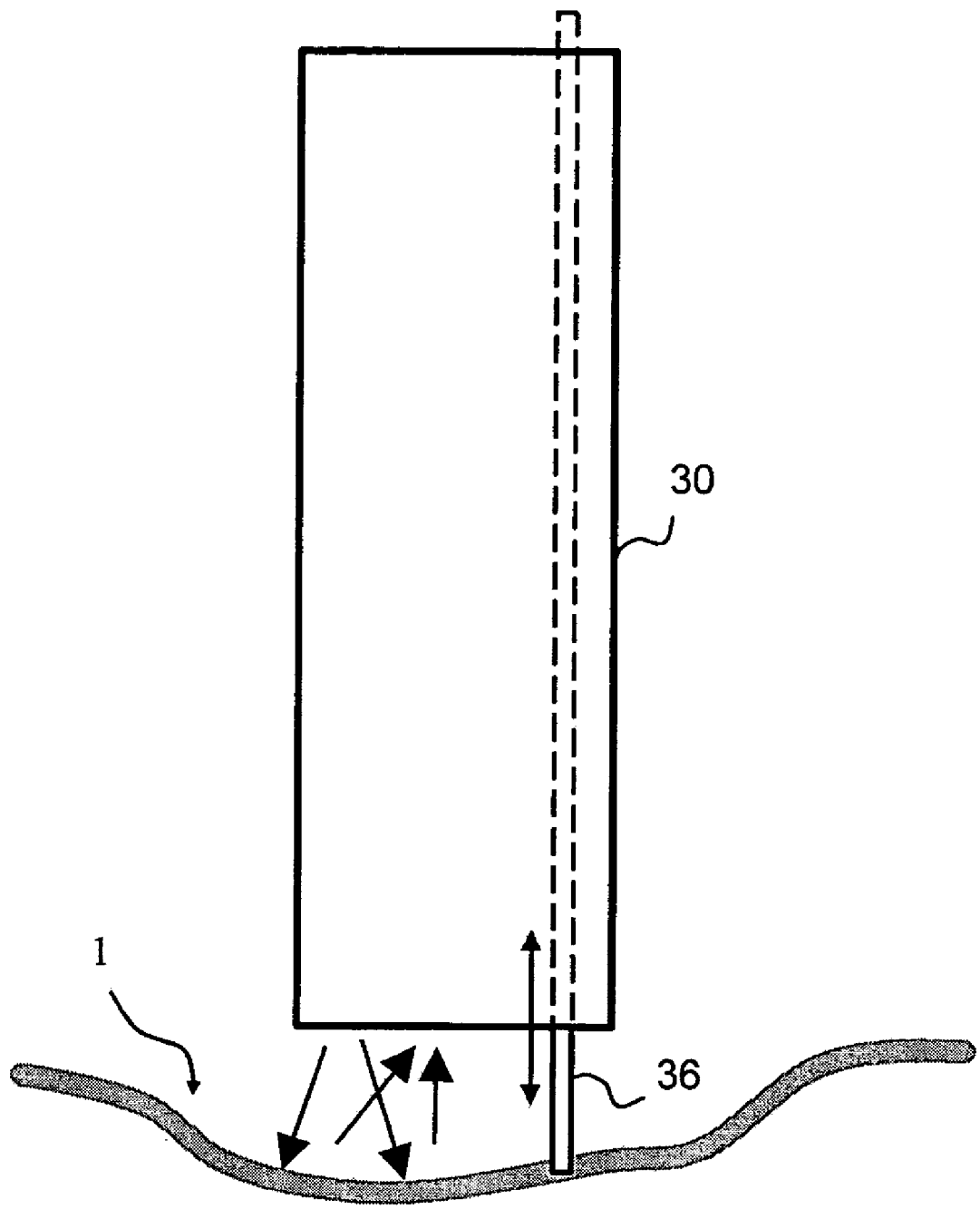
FIG. 3 shows a method for maintaining the distance from the distal end of an endoscope to a diagnostic object according to the prior art.

Meanwhile, the present invention compensates for the change in fluorescent brightness according to the distance change for accurate quantitative analysis of fluorescent brightness. FIG. 2 shows the change in brightness of fluorescent light and reflected excitation light when the distance from the distal end of the endoscope to a diagnostic object changes. It is clear from the drawing that the intensity of reflected excitation light and fluorescent light decreases at almost the same ratio according to the distance. By automatically adjusting the gain during amplification of reflected excitation light for uniform reflected excitation light and the amplification gain of fluorescent light with the same changing ratio of the gain of the reflected excitation light, therefore, a uniform intensity of fluorescent light can be obtained regardless of the distance change. Such a function is performed by the first and second video signal analog processing blocks 62 and 63 which process the first optical detection signal and is realized by a gain control unit for controlling the signal amplification gain value to adjust the brightness of images detected by the first optical detection chip, a first amplification unit for amplifying the first optical detection signal based on the signal amplification gain value, and a second amplification unit for amplifying the second optical detection signal based on a gain value determined to have the same level of changing ratio with the signal amplification gain value of the first amplification unit.

The image composition unit of the fluorescent endoscope system according to the present invention causes the input switch to toggle between the first and second states according to the common synchronization signal and causes signals corresponding to each frame of the first and second optical detection signals to be alternatively inputted for minimized data loss of composed images.

Figure 8:
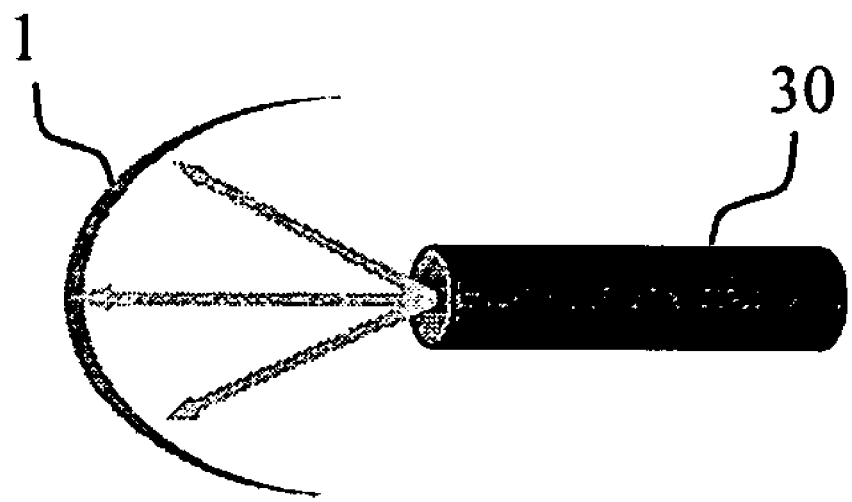
FIG. 8 shows the irregularity of image brightness caused by the geometry of diagnostic objects.
Figure 8:
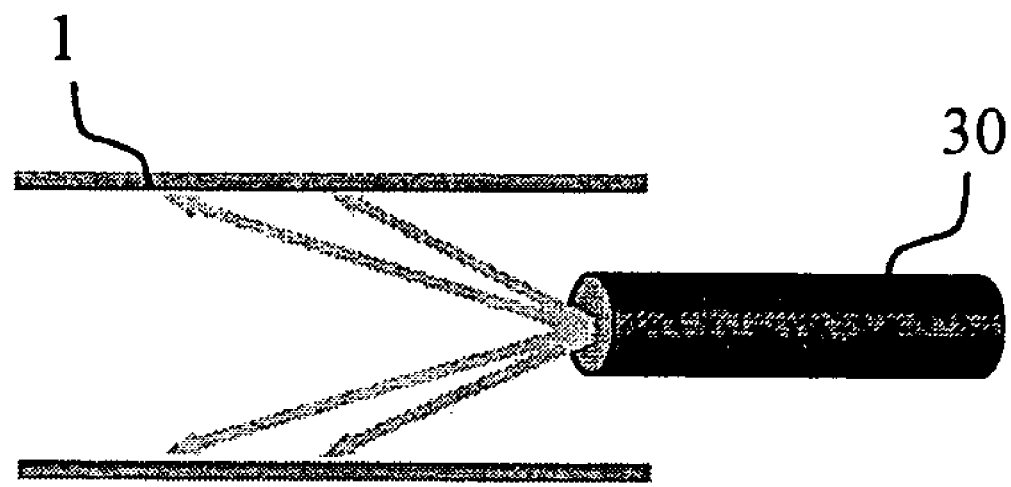
Figure 9:
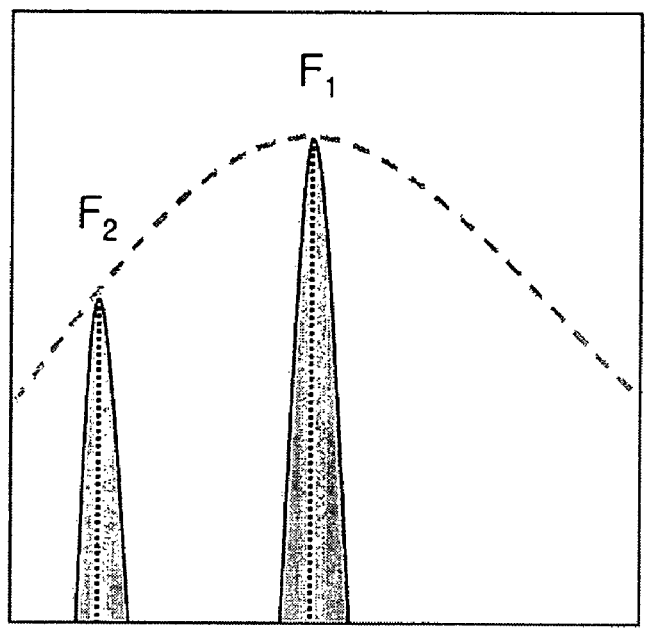
FIG. 9 shows the change in intensity of fluorescent light and reflected light obtained in the case of a curved diagnostic object according to position.
Figure 9:
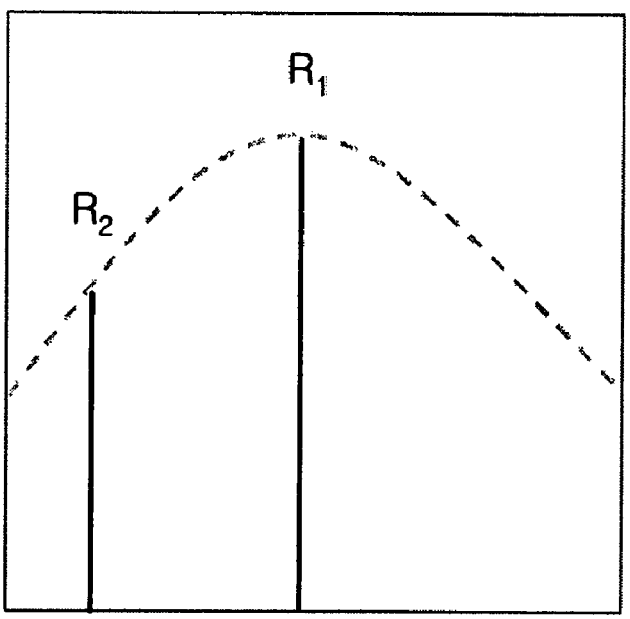

FIG. 8 shows the irregularity of image brightness caused by the geometry of diagnostic objects and FIG. 9 shows the change in intensity of fluorescent light and reflected light obtained in the case of a curved diagnostic object according to position. In many cases, the inner surface of an organ to be diagnosed is a concave surface, particularly of a cup or tube shape, as shown in FIG. 8. Points on the outer edge are positioned closer to the axis of the endoscope than central points in this case and the optical signal from the edge of the view of field of the endoscope is larger than that from points positioned at the center. Such an image is often observed in the esophagus. As a result, the fluorescent brightness of points on the edge may be perceived by the endoscope to be larger than the actual value. Such an error of fluorescent brightness caused by the geometry of an organ makes the diagnosis based on quantitative analysis of fluorescent light inaccurate.

The fluorescent endoscope system according to the present invention can solve the problem of irregularity of illumination and that of the degree of light collection in the field of view of the endoscope through calibration using reference specimens as in the prior art. Error caused by the geometry of the interior of an organ, however, varies depending on the surface shape of a diagnostic object and cannot be compensated for using reference specimens. In order to compensate for such an error of fluorescent intensity distribution caused by the geometry of the interior of an organ, the fluorescent endoscope system according to the present invention makes use of the fact the influence of the geometry on reflected excitation light is equal to that on fluorescent light.

First, it is assumed that the whole surface of the diagnostic object has the same degree of diffusive reflection. In this case, fluorescent intensity may be perceived to have different sensitivities depending on the position of each point in the field of view as shown in part (a) of FIG. 9. Comparing the fluorescent intensity F1 of a point at the center and the fluorescent intensity F2 of a point on the edge of the field of view, the latter is closer to the endoscope and is larger than the former. Signal intensities R1 and R2 of reflected excitation light can be respectively obtained from a first optical detection signal on the same point. Under the assumption that the degree of diffusive reflection is the same on the whole surface of the diagnostic object, the influence of the geometry on the distribution of reflected excitation light can be expressed as a ratio: R2/R1=L. Particularly, the value of reflected excitation light on the edge is observed to be L times larger than that at the center due to the influence of the geometry. In the same manner, the fluorescent intensity F2 of a point on the edge is observed to be L times larger than that at the center. Therefore, the actual fluorescent intensity F2' on the edge can be obtained by dividing the observed intensity F2 by L. Such data compensation is performed by a data processing unit provided in the computer 80, which may be realized as a program run by the processor of the computer 80 or as hardware.

Figure 6:
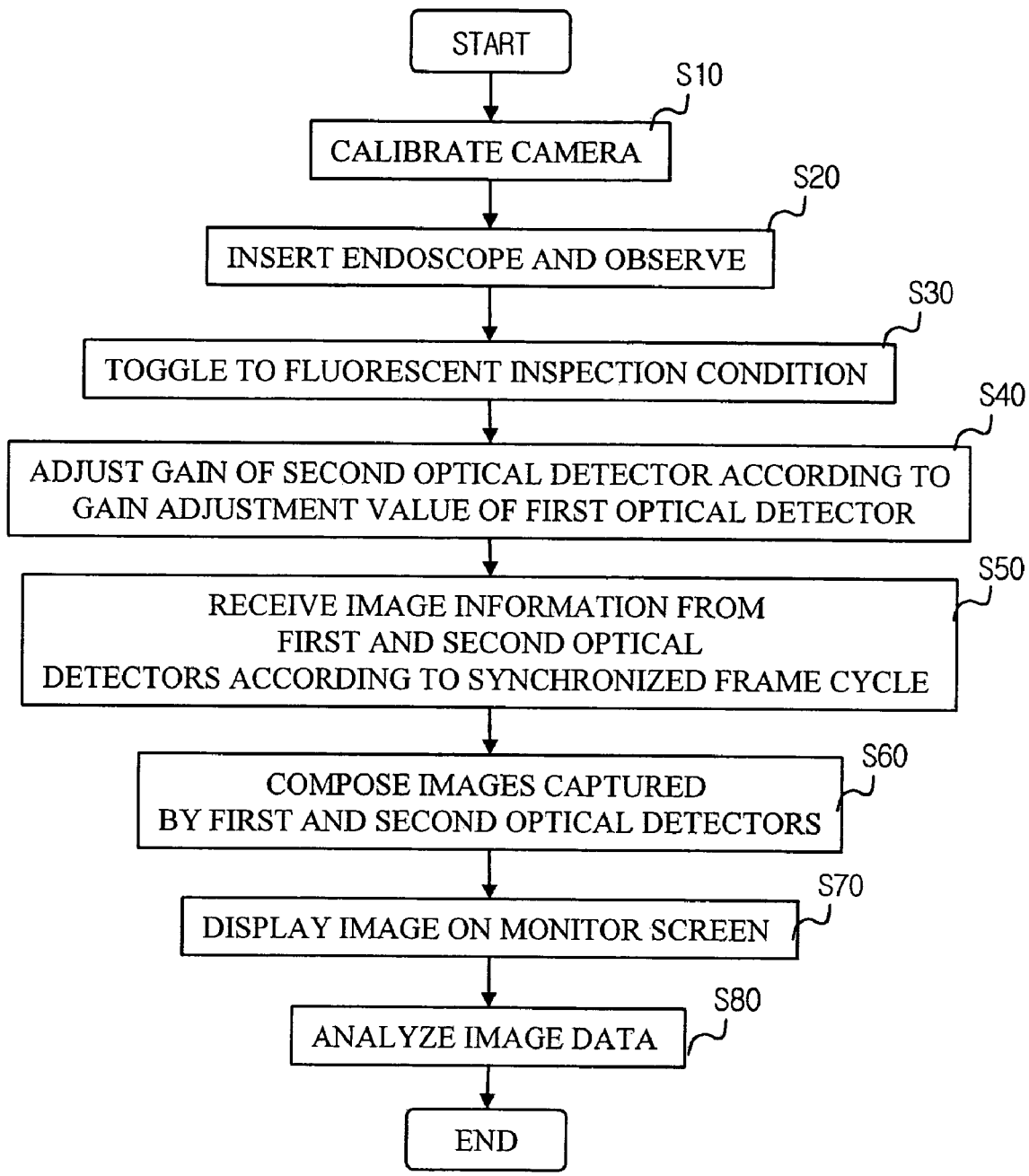
FIG. 6 is a flowchart showing a method for imaging a diagnostic object with a system according to an embodiment of the present invention.

A method for imaging a diagnostic object using the fluorescent endoscope system according to the present invention will now be described. FIG. 6 is a flowchart showing a method for imaging a diagnostic object with the system according to an embodiment of the present invention. The system is first calibrated S10 before it is used to inspect an internal tissue of the body. The calibration is performed using white and fluorescent samples 111 and 112 spaced a predetermined distance from the distal end of the endoscope.

Figure 7:
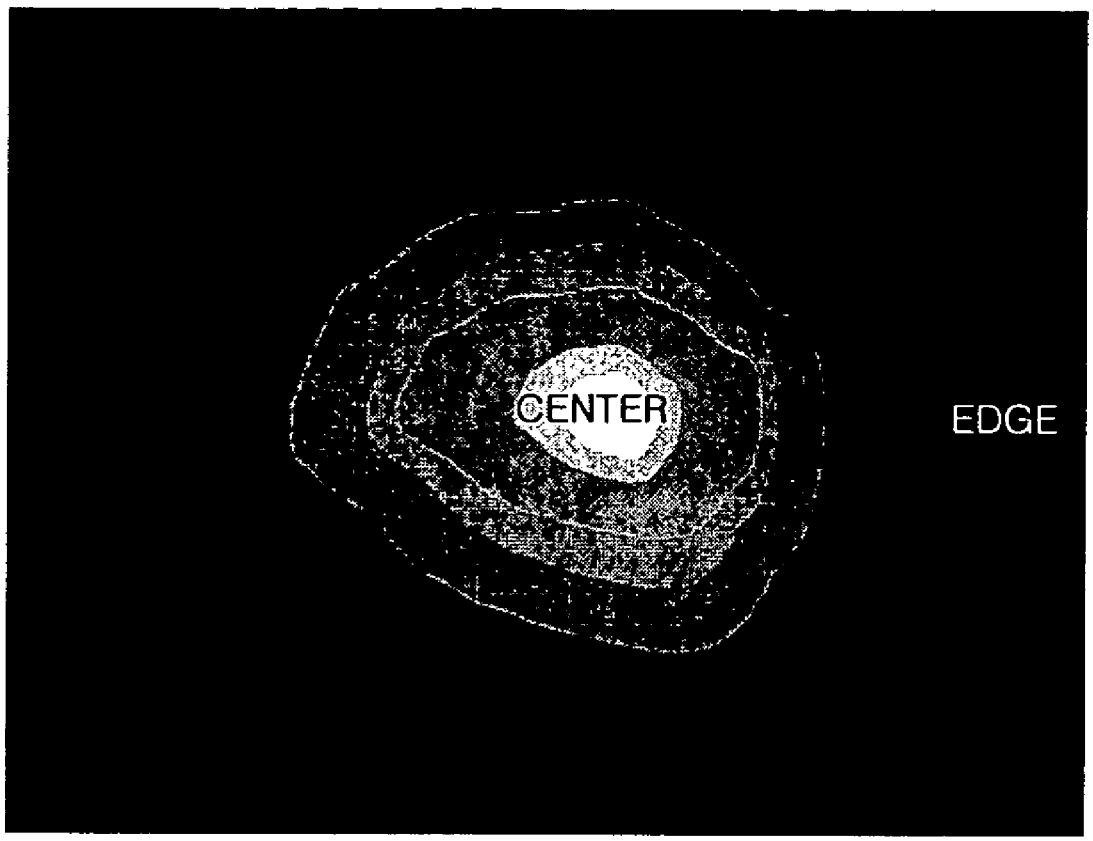
FIG. 7 shows the irregularity of image brightness caused by the irregularity of illumination.

For example, the endoscope system according to the present invention is set in a normal endoscope mode for calibration and the distal end of the endoscope assembly 30 is inserted into a calibration block 110. A white sample 111 having at least 90% diffusive reflection coefficient in the spectrum range of visible rays is positioned in the field of view of the endoscope. An image is then obtained as shown in FIG. 7 and is stored for calibration of a first optical detection signal. The endoscope system is then toggled to a fluorescent observation mode and a fluorescent sample 112 having a maximum fluorescent brightness that can be obtained from the diagnostic object is positioned in the field of view of the endoscope. An image is obtained as shown in FIG. 7 and is stored for calibration of a second optical detection signal.

After calibration is over, the distal end of the endoscope 30 is inserted into the diagnostic object of a patient and visual inspection is performed in a normal endoscope mode S20. If tissues having abnormal morphological structure or color are observed from the diagnostic object, it is doubtful that it has tumors. In this case, the system is toggled to a fluorescent observation mode for detailed inspection of the dubious parts S30.

In the fluorescent observation mode, the image of fluorescent light generated from excitation light at the dubious tissue is captured by the monochrome optical detection chip 52 and the image of reflected excitation light is captured by the color optical detection chip 51. The image brightness of fluorescent light and reflected excitation light from the tissue is constantly maintained by an automatic gain control AGC circuit even when the measurement distance from the distal end of the endoscope to the diagnostic object varies S40. The automatic gain control is performed by amplification gain control based on the analysis of the first optical detection signal level. The value of used amplification gain is also used as the gain for amplification of the second optical detection signal.

Each frame of the first optical detection signal and that of the second optical detection signal obtained by means of the common synchronization signal are alternatively selected to compose a image having superimposed images of fluorescent light and reflected excitation light S60. The composed frames are displayed on the monitor S70.

The first and second optical detection signals are then analyzed to compensate for the error of fluorescent intensity caused by geometrical influence. The fluorescent brightness of dubious parts of the given tissue and that of an apparently healthy tissue positioned adjacent to it are compared to determine the fluorescent brightness contrast. The resulting fluorescent brightness data is used for diagnosis through quantitative evaluation of fluorescent light.

In the two-chip integration image detection module 50 of the present invention, the electronic shutter speed of the first and second optical detection chips 51 and 52 can be independently adjusted. Accordingly, fluorescent light can be observed under image background of bright excitation light and the dynamic range of the recording channel of excited reflection light can be enlarged.

In order to adjust the detection intensity against incident optical signals, the optical detector (e.g., CCD) uses an electronically controlled shutter to control the exposure time. If exposure to incident light occurs for a minimum period of time using the electronically controlled shutter, it is possible to prevent signal charge from being excessively accumulated on pixels of the optical detection device, even in the case of the brightest light. This increases the illumination of excitation light and the brightness of fluorescent light. The amount of light (illumination) received by the optical detection surface of the CCD camera can be increased by thousands of times by adjusting the speed of the electronic shutter. Particularly, the luminance can be drastically increased by shortening the exposure time of the electronic shutter.

Such a function is particularly important when illumination light of high luminance must be used for fluorescent excitation or photodynamic therapy (PDT) and reflection light must be observed while preventing signal charge of pixels of the optical detector from being excessively accumulated at the color channel for observing reflection light and overflowing to the periphery. When fluorescent light having weaker intensity is to be simultaneously observed, in contrast, a high-sensitivity condition for accumulating signal electrons from a number of frames is used. The system having a two-chip integration image processing module according to the present invention can drastically increase the dynamic range, during image detection, through independent control of the shutter exposure time under a synchronized condition.

According to the fluorescent endoscope system of the present invention, it is possible to provide a frame having synchronized images of reflected excitation light and fluorescent light composed with high accuracy without performing complex calculation algorithm for image composition.

It is possible to accurately maintain the brightness of fluorescent images, even when the distance between the diagnostic object and the distal end of the endoscope varies, for accurate diagnosis. Accordingly, it is unnecessary to fix the distance between the diagnostic object and the distal end of the endoscope with a tool inserted into the endoscope as in the prior art.

The first and second optical detection chips are driven by a single integral control module. This makes the system simple and avoids use of redundant components.

The shutter speed of the first and second optical detection chips is independently controlled for more sensitive observation of faint fluorescent light than reflected excitation light. This enlarges the dynamic range during recording excited reflection light.

The ratio (fluorescent brightness contrast coefficient) of fluorescent brightness of a normal tissue to that of a dubious tissue enables accurate quantitative diagnosis having reduced influence of individual peculiarity of each living body to medicine. The fluorescent endoscope system according to the present invention also makes it possible to compensate for the influence of the geometry of the interior of an organ for more accurate diagnosis based on the comparison of fluorescent intensity.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A fluorescent endoscope system for imaging an internal tissue of a body comprising:
   an optical source module for providing excitation light;
   an endoscope assembly having an optical transmission path for transmitting light provided from the optical source module to a diagnostic object and an optical detection module for transmitting reflection light and fluorescent light from the diagnostic object;
   an optical path split means for splitting the path of the reflection light and fluorescent light transmitted from the endoscope assembly; and
   a two-chip integration image detection module having a first optical detection chip for detecting the reflection light and outputting a first optical detection signal, a second optical detection chip for detecting the fluorescent light and outputting a second optical detection signal, a gain control unit for controlling a signal amplification gain value to adjust the brightness of images detected by the first and second optical detection chips, a first amplification unit for amplifying the first optical detection signal according to the signal amplification gain value, and a second amplification unit for amplifying the second optical detection signal according to the signal amplification gain value; and
   a digital control unit for providing the first and second optical detection chips with a common synchronization signal so that the timing of each frame of the first and second optical detection signals coincides, wherein the gain control unit maintains the brightness of images output from the image detection module regardless of a change in a distance between a distal end of the endoscope assembly and the diagnostic object by amplifying the first and second detection signals according to the signal amplification gain value controlled based on the reflection light detected by the first optical detection chip.

2. The fluorescent endoscope system as claimed in claim 1, further comprising an image composition unit provided with an input switch having a first state for selectively receiving the first optical detection signal and a second state for selectively receiving the first and second optical detection signals and adapted to alternatively receive data of some frames of output of the first optical detection signal and data of some frames of output of the second optical detection signal to convert them and display a composite image.

3. The fluorescent endoscope system as claimed in claim 2, wherein the image composition unit causes the input switch to toggle between the first and second states according to the common synchronization signal and causes signals corresponding to each frame of the first and second optical detection signals to be alternatively inputted for minimized data loss of the composite image.

4. The fluorescent endoscope system as claimed in claim 1, further comprising a data processing unit which uses the ratio of image brightness (L1) of the reflection light of a first point in the field of view of the endoscope to image brightness (L2) of the reflection light of a second point and compensates for obtained image brightness (F2) of the fluorescent light of the second point based on image data obtained by the two-chip integration image detection module.

5. The fluorescent endoscope system as claimed in claim 4, wherein the first point is a reference point set in a predetermined position on the image and the data processing unit is adapted to compensate for the measurement error of fluorescent intensity observed through the endoscope when the diagnostic object has a curved surface.

6. The fluorescent endoscope system as claimed in claim 1, wherein the optical source module has an optical source for providing illumination light and excitation light.

7. The fluorescent endoscope system as claimed in claim 6, wherein the illumination light and the excitation light are provided by two separate lamps.

8. The fluorescent endoscope system as claimed in claim 7, wherein the optical source for illumination light is a metal-halide lamp and the optical source for excitation light is a mercury lamp.

9. The fluorescent endoscope system as claimed in claim 6, wherein the illumination light and the excitation light are provided by a single lamp.

10. The fluorescent endoscope system as claimed in claim 9, wherein the single lamp is a metal-halide lamp.

11. The fluorescent endoscope system as claimed in claim 9, wherein the single lamp is an LED.

12. The fluorescent endoscope system as claimed in claim 9, wherein the single lamp is a xenon lamp.

13. The fluorescent endoscope system as claimed in claim 1, wherein the endoscope assembly is a flexible or hard endoscope.

14. The fluorescent endoscope system as claimed in claim 1, wherein the endoscope assembly is an optical fiber or an electronic endoscope.

15. The fluorescent endoscope system as claimed in claim 1, wherein the optical path split means is adapted to toggle between a first mode for transmitting all light to the first optical detection chip and a second mode for separately transmitting the reflection and fluorescent light to the first and second optical detection chips, respectively.

16. The fluorescent endoscope system as claimed in claim 15, wherein the optical path split means has a dichroic optical splitter and a driving unit for driving the dichroic optical splitter.

17. The fluorescent endoscope system as claimed in claim 15, further comprising an external switch for easy toggling between the first and second modes by controlling the optical path split means.

18. The fluorescent endoscope system as claimed in claim 17, wherein the external switch is a pedal.

19. The fluorescent endoscope system as claimed in claim 1, further comprising an optical coupling means coupled between the endoscope assembly and the optical path split means and having a projection objective lens for projecting images on the optical detection surface of the first and second optical detection chips.

20. The fluorescent endoscope system as claimed in claim 19, wherein the optical coupling means has a spatial low-pass filter for suppressing a predetermined spatial frequency to remove moir effect.

21. The fluorescent endoscope system as claimed in claim 20, wherein the spatial low-pass filter is mounted in such a manner that it can rotate about an optical axis for fine adjustment in the direction of optical fiber bundles arranged in a flexible endoscope.

22. The fluorescent endoscope system as claimed in claim 1, wherein the excitation light has a spectrum range of 380-580 nm.

23. The fluorescent endoscope system as claimed in claim 1, wherein the fluorescent light has a wavelength of 600 nm or more.

24. The fluorescent endoscope system as claimed in claim 1, further comprising an optical shield filter positioned in front of the second optical detection chip to allow only the fluorescent light to pass through.

25. The fluorescent endoscope system as claimed in claim 24, wherein the optical shield filter is adapted to absorb light of 600 nm or less.

26. The fluorescent endoscope system as claimed in claim 1, further comprising an analog digital conversion unit for converting the first and second optical detection signals into digital signals.

* * * * *

UNITED STATES PATENT AND TRADEMARK OFFICE
CERTIFICATE OF CORRECTION

PATENT NO. : 7,635,330 B2
APPLICATION NO. : 11/072995
DATED : December 22, 2009
INVENTOR(S) : Kang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1182 days.

Signed and Sealed this

Ninth Day of November, 2010

David J. Kappos
*Director of the United States Patent and Trademark Office*